United States Patent
Schroeder et al.

(10) Patent No.: US 12,239,427 B2
(45) Date of Patent: Mar. 4, 2025

(54) HEARTRATE TRACKING TECHNIQUES

(71) Applicant: Apple Inc., Cupertino, CA (US)

(72) Inventors: Christian Schroeder, Palo Alto, CA (US); Divya Padmanabhan, Cupertino, CA (US); Erno H. Klaassen, Los Altos, CA (US); Evan R. Doll, Los Gatos, CA (US); Ian R. Shapiro, San Francisco, CA (US); Jay Kriz Blahnik, Venice, CA (US); Roxanne B. Brittain, Berkeley, CA (US); Stephen J. Waydo, Saratoga, CA (US); Joefrey S. Kibuule, San Francisco, CA (US); Alexa VanHattum, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/210,826

(22) Filed: Jun. 16, 2023

(65) Prior Publication Data
US 2023/0320605 A1   Oct. 12, 2023

Related U.S. Application Data

(60) Division of application No. 17/133,138, filed on Dec. 23, 2020, now Pat. No. 11,690,522, which is a
(Continued)

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0255* (2013.01); *A61B 5/1123* (2013.01);
(Continued)

(58) Field of Classification Search
None
See application file for complete search history.

(56) References Cited

U.S. PATENT DOCUMENTS

| 5,483,261 | A | 1/1996 | Yasutake |
| 5,488,204 | A | 1/1996 | Mead et al. |

(Continued)

FOREIGN PATENT DOCUMENTS

| CN | 101493865 A | 7/2009 |
| CN | 102138789 A | 8/2011 |

(Continued)

OTHER PUBLICATIONS

"Notice of Decision to Grant," mailed from the Chinese Patent Office on Aug. 28, 2023 in application No. 201880030449.9. 9 pages (includes brief description and English translation of allowed claims).

(Continued)

*Primary Examiner* — Mallika D Fairchild
(74) *Attorney, Agent, or Firm* — Kilpatrick Townsend & Stockton LLP

(57) ABSTRACT

An example technique may include tracking motion of a user wearing the wearable device using at least first sensors of one or more sensors of the wearable device. The technique may also include tracking a physical state of the user using at least second sensors of the one or more sensors of the wearable device. The technique may also include determining whether an application of the wearable device has been launched. The technique may also include determining an action category of the user based at least in part on at least one of the motion of the user, the physical state of the user, or whether the application has been launched. The technique may also include collecting heartrate data of the user. The
(Continued)

technique may also include categorizing the heartrate data based at least in part on the determined action category.

20 Claims, 9 Drawing Sheets

Related U.S. Application Data continuation of application No. 15/843,623, filed on Dec. 15, 2017, now Pat. No. 10,874,313.

(60) Provisional application No. 62/514,882, filed on Jun. 4, 2017.

(51) Int. Cl.
  *A61B 5/0255* (2006.01)
  *A61B 5/11* (2006.01)
  *G16H 10/60* (2018.01)

(52) U.S. Cl.
  CPC ............ *A61B 5/681* (2013.01); *A61B 5/7475* (2013.01); *G16H 10/60* (2018.01); *A61B 5/02416* (2013.01); *A61B 5/1118* (2013.01); *A61B 5/486* (2013.01); *A61B 5/7285* (2013.01); *A61B 5/7435* (2013.01)

(56) References Cited

U.S. PATENT DOCUMENTS

| | | | |
|---|---|---|---|
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi et al. |
| 7,184,064 | B2 | 2/2007 | Zimmerman et al. |
| 7,662,065 | B1 | 2/2010 | Kahn et al. |
| 7,663,607 | B2 | 2/2010 | Hotelling et al. |
| 8,392,735 | B2 | 3/2013 | Mucignat et al. |
| 8,479,122 | B2 | 7/2013 | Hotelling et al. |
| 9,009,516 | B1 | 4/2015 | Gabayan et al. |
| 9,224,311 | B2 | 12/2015 | Yeh et al. |
| 10,327,674 | B2 | 6/2019 | Hong et al. |
| 10,874,313 | B2 | 12/2020 | Schroeder et al. |
| 2004/0015103 | A1 | 1/2004 | Aminian et al. |
| 2006/0197753 | A1 | 9/2006 | Hotelling |
| 2011/0035292 | A1 | 2/2011 | Boesel |
| 2012/0274508 | A1 | 11/2012 | Brown et al. |
| 2013/0324855 | A1 | 12/2013 | Lisogurski et al. |
| 2014/0197965 | A1 | 7/2014 | Park et al. |
| 2014/0240122 | A1 | 8/2014 | Roberts et al. |
| 2014/0275852 | A1 | 9/2014 | Hong et al. |
| 2014/0371886 | A1* | 12/2014 | Jain ........................ G06V 40/23 700/91 |
| 2015/0119760 | A1 | 4/2015 | Wisbey et al. |
| 2015/0342533 | A1 | 12/2015 | Kelner |
| 2015/0347499 | A1 | 12/2015 | Keen et al. |
| 2016/0029898 | A1 | 2/2016 | LeBoeuf et al. |
| 2016/0038045 | A1 | 2/2016 | Shapiro |
| 2016/0058337 | A1 | 3/2016 | Blahnik et al. |
| 2016/0058356 | A1 | 3/2016 | Raghuram et al. |
| 2016/0058378 | A1 | 3/2016 | Wisbey et al. |
| 2016/0081627 | A1 | 3/2016 | McGloin et al. |
| 2016/0091952 | A1 | 3/2016 | Xu et al. |
| 2016/0150978 | A1 | 6/2016 | Yuen et al. |
| 2016/0242659 | A1 | 8/2016 | Yamashita et al. |
| 2016/0261528 | A1* | 9/2016 | Blahnik ................. A61B 5/681 |
| 2016/0324432 | A1 | 11/2016 | Ahmed et al. |
| 2016/0368965 | A1 | 12/2016 | Mahr et al. |
| 2016/0374567 | A1 | 12/2016 | Breslow et al. |
| 2017/0056722 | A1* | 3/2017 | Singh ................... A61B 5/1118 |
| 2017/0075737 | A1 | 3/2017 | Kim et al. |
| 2017/0128019 | A1 | 5/2017 | Shao et al. |
| 2017/0188847 | A1 | 7/2017 | Ahmed et al. |
| 2017/0337349 | A1 | 11/2017 | Cronin |
| 2017/0354795 | A1* | 12/2017 | Blahnik ................. G16H 20/70 |
| 2018/0156660 | A1 | 6/2018 | Turgeon et al. |
| 2018/0344178 | A1 | 12/2018 | Deng et al. |
| 2020/0143258 | A1 | 5/2020 | Kanner et al. |
| 2021/0068714 | A1 | 3/2021 | Crowley et al. |

FOREIGN PATENT DOCUMENTS

| | | |
|---|---|---|
| CN | 102151136 A | 8/2011 |
| CN | 105549720 A | 5/2016 |
| CN | 105705090 A | 6/2016 |
| CN | 105960196 A | 9/2016 |
| CN | 105996987 A | 10/2016 |
| CN | 106502369 A | 3/2017 |
| JP | 2000163031 A | 6/2000 |
| JP | 2002342033 A | 11/2002 |

OTHER PUBLICATIONS

"Notification of Second Office Action," mailed May 28, 2023, in Chinese Patent Application No. 2018800304499. 9 pages (includes English translation).
U.S. Appl. No. 15/843,623 , "First Action Interview Pilot Program Pre-Interview Communication", Jan. 21, 2020, 9 pages.
U.S. Appl. No. 15/843,623 , "Notice of Allowance", Apr. 7, 2020, 10 pages.
U.S. Appl. No. 15/843,623 , "Notice of Allowance", Aug. 19, 2020, 7 pages.
U.S. Appl. No. 15/991,798 , "Advisory Action", Jun. 3, 2021, 2 pages.
U.S. Appl. No. 15/991,798 , "Final Office Action", Feb. 26, 2021, 10 pages.
U.S. Appl. No. 15/991,798 , "Non-Final Office Action", Nov. 17, 2020, 11 pages.
U.S. Appl. No. 15/991,798 , "Non-Final Office Action", May 6, 2020, 8 pages.
U.S. Appl. No. 15/991,798 , "Notice of Allowance", Jul. 15, 2021, 8 pages.
U.S. Appl. No. 17/133,138 , "Non-Final Office Action", Sep. 12, 2022, 11 pages.
U.S. Appl. No. 17/133,138 , "Notice of Allowance", Feb. 23, 2023, 7 pages.
U.S. Appl. No. 17/133,138 , "Notice of Allowance", Feb. 2, 2023, 8 pages.
Chinese Patent Application No. 201880030449.9 , "Office Action", Nov. 21, 2022, 15 pages.
European Patent Application No. 18720442.5 , "Intention to Grant", Nov. 24, 2020, 8 pages.
European Patent Application No. 18720442.5 , "Notice of Decision to Grant", Apr. 9, 2021, 2 pages.
Lee et al., "A Multi-touch Three Dimensional Touch-sensitive Tablet", Proceedings of CHI: Association for Computing Machinery Conference on Human Factors in Computing Systems, Apr. 1985, pp. 21-25.
International Patent Application No. PCT/US2018/025061 , "International Preliminary Report on Patentability", Dec. 19, 2019, 11 pages.
International Patent Application No. PCT/US2018/025061 , "International Search Report and Written Opinion", Aug. 10, 2018, 17 pages.
International Patent Application No. PCT/US2018/025061 , "Invitation to Pay Additional Fees and, Where Applicable, Protest Fee", Jun. 18, 2018, 10 pages.
International Patent Application No. PCT/US2022/030491 , "International Search Report and Written Opinion", Sep. 5, 2022, 14 pages.
Rubine , "Combining Gestures and Direct Manipulation", CHI '92: Proceedings of the SIGCHI Conference on Human Factors in Computing Systems, May 3-7, 1992, pp. 659-660.

(56) References Cited

OTHER PUBLICATIONS

Rubine, "The Automatic Recognition of Gestures", CMU-CS-91-202, Submitted in Partial Fulfillment of the Requirements for the Degree of Doctor of Philosophy in Computer Science, Dec. 1991, 285 pages.

Westerman, "Hand Tracking, Finger Identification, and Chordic Manipulation on a Multi-Touch Surface", A dissertation submitted to the faculty of the University of Delaware in Partial Fulfillment of the Requirements for the Degree of Doctor of Philosophy in Electrical Engineering, 1999, 363 pages.

\* cited by examiner

HEARTRATE TRACKING TECHNIQUES

CROSS-REFERENCES TO RELATED APPLICATIONS

This application is a divisional of U.S. patent application Ser. No. 17/133,138, filed Dec. 23, 2020, entitled "Heartrate Tracking Techniques," which is a continuation of U.S. patent application Ser. No. 15/843,623 (U.S. Pat. No. 10,874,313), filed Dec. 15, 2017, entitled "Heartrate Tracking Techniques," which claims the benefit of U.S. Provisional Patent Application No. 62/514,882, filed Jun. 4, 2017, entitled "Heartrate Tracking Techniques," the contents of all of which are herein incorporated by reference.

BACKGROUND

The number of wearable computing devices has grown drastically over the years. Many of these wearable devices are configured to collect heartrate data of a user. Various techniques for collecting heartrate data have been developed, with some providing better results than others. However, various techniques do not work well in certain situations. Interference with other data collected by the wearable device, as well as other factors, have made many of these wearable heartrate detecting devices inaccurate and/or unusable in certain situations. Additionally, it is often difficult to make sense of the different heartrate information that is collected.

SUMMARY

Embodiments of the present disclosure can provide systems, methods, and computer-readable medium for implementing heartrate tracking techniques. In some examples, a wearable computing device (e.g., a smart watch or other device with sensors that can detect a user's heartrate) may be used to collect heartrate data of a user, determine appropriate algorithms to use for processing the data based at least in part on context, track the processed data, and present the heartrate data in a meaningful manner.

In some embodiments, a computer-implemented method for implementing various heartrate tracking techniques may be provided. The method may include detecting, by a wearable computing device, a launch of a first application comprising a first application user interface. The method may also comprise detecting a first user input on the first application user interface corresponding to a first setting criteria and/or collecting first heartrate metrics using a first technique during a first period. The method may also comprise tracking the first heartrate metrics according to the first setting criteria during the first period. In some examples, the method may also comprise detecting a launch of a second application comprising a second application user interface and/or detecting a second user input on the second application user interface corresponding to a second setting criteria different from the first setting criteria. The method may also comprise collecting second heartrate metrics using a second technique during a second period and/or tracking the second heartrate metrics according to the second setting criteria during the second period.

In some embodiments, the first setting criteria may be for completing a first application session associated with the first application, and the second setting criteria may be for completing a second application session associated with the second application. Additionally, the first heartrate metrics may be tracked according to the first setting criteria during the first period based at least in part on initiation of the first application session and/or the first period may correspond to the first application session, and the second period may correspond to the second application session. The first and second heartrate metrics may be tracked differently during each of the first session and the second session, respectively. Further, the first technique may be determined based at least in part on a first context of the first application, and the second technique may be determined based at least in part on a second context of the second application.

In some embodiments, a system for implementing various heartrate tracking techniques may be provided. The system may comprise one or more memories configured to store computer-executable instructions, one or more sensors configured to sense biometric data of a user, and one or more processors in communication with the one or more memories. The processors may be configured to execute the computer-executable instructions to perform operations. The operations may include tracking motion of a user wearing the wearable device using at least first sensors of the one or more sensors and/or tracking a physical state of the user using at least second sensors of the one or more sensors. The operations may also include determining whether an application of the wearable device has been launched and/or determining an activity category of the user based at least in part on at least one of the motion of the user, the physical state of the user, or whether the application has been launched. The operations may be further configured to include collecting heartrate data of the user categorizing the heartrate data based at least in part on the determined category.

In some instances, the heartrate data of the user may be collected based at least in part on the determined activity category. Additionally, the heartrate data of the user may be categorized as sedentary when the motion of the user is below a threshold and no application has been launched. In some instances, the heartrate data of the user may be categorized as breathing when the application has been launched and the application comprises breathing instructions for the user and/or the heartrate data of the user may be categorized as workout when the motion of the user is above a threshold, the application has been launched, and the application is configured to track the physical state of the user.

In some embodiments, a computer-readable medium may be provided. The computer-readable medium may include computer-executable instructions that, when executed by a processor, cause the processor to perform operations. The operations may include detecting first category of activity and/or determining a first collection technique for collecting first heartrate metrics for the first category of activity. The operations may also include collecting the first heartrate metrics according to the first collection technique during a first period. In some instances, the operations may include detecting a second category of activity and/or determining a second collection technique different from the first collection technique for collecting second heartrate metrics for the second category of activity. In some embodiments, the operations may further include collecting the second heartrate metrics according to the second collection technique during a second period and/or tracking the first heartrate metrics and the second heartrate metrics for the first and second periods, respectively.

In some embodiments, the first and second heartrate metrics may be tracked differently during each of the first period and the second period, respectively. In some instances, the first category of activity may comprise a first setting criteria, and the second category of activity may comprise a second setting criteria. In some embodiments, the first heartrate metrics may be further collected according to the first setting criteria, and the second heartrate metrics may be further collected according to the second setting criteria and/or the first setting criteria may be for completing a first session associated with a first application, and the second setting criteria may be for completing a second session associated with a second application. In some cases, the operations may further include detecting initiation of the second session, and tracking the second heartrate metrics according to the second setting criteria during the second period in response to the detection of the initiation of the second session. Additionally, in some instances, the first collection technique may comprise utilizing first sensors of a wearable computing device, and the second collection may comprise utilizing second sensors of the wearable computing device. Further, the wearable computing device may comprise a watch capable of collecting biometric data of a user and/or the first collection technique may be determined based at least in part on a first type of the first category of activity, and the second collection technique may be determined based at least in part on a second type of the second category of activity.

The following detailed description together with the accompanying drawings will provide a better understanding of the nature and advantages of the present disclosure.

DETAILED DESCRIPTION

Figure 1:
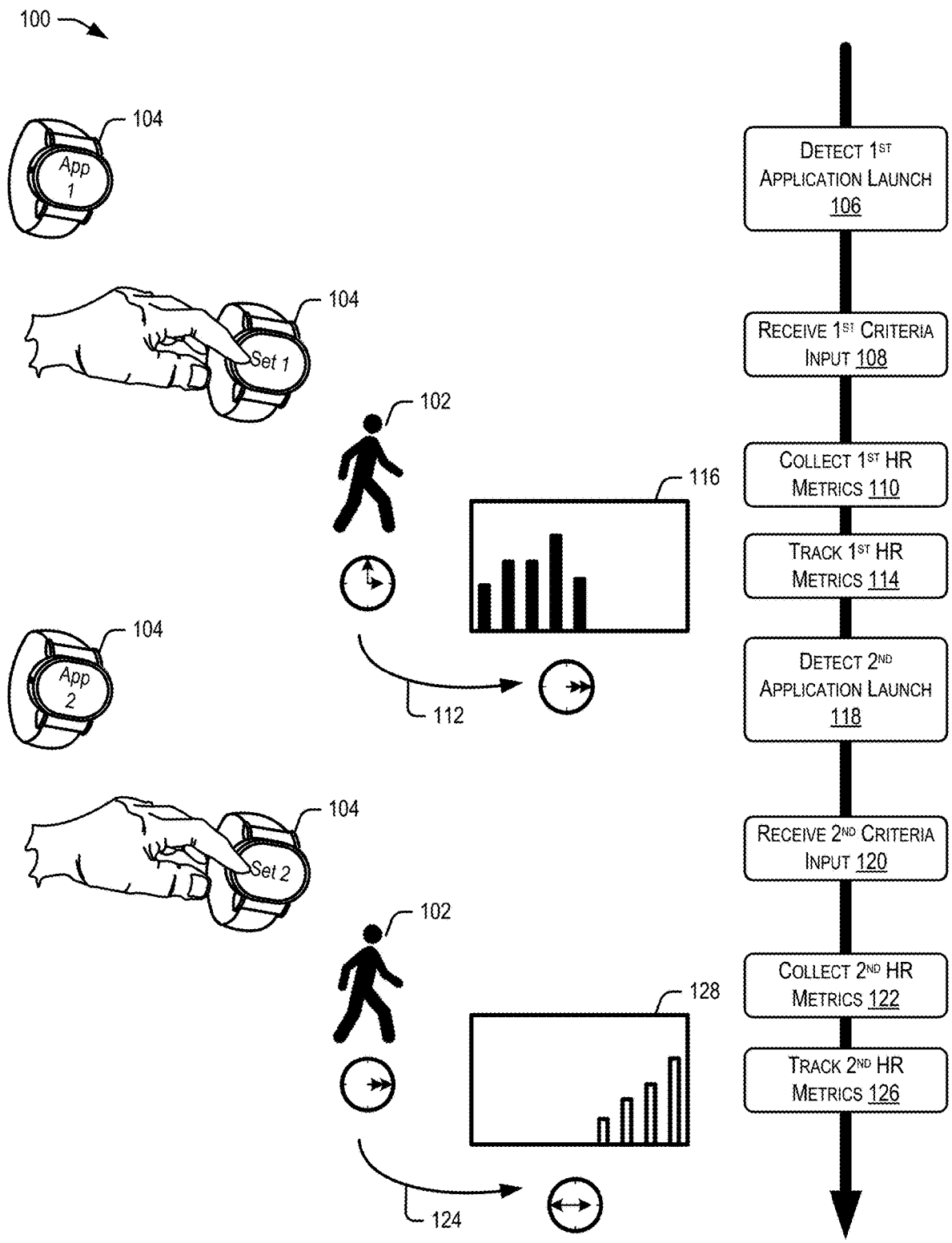
FIG. 1 is a simplified block diagram illustrating an example flow for providing various heartrate tracking techniques as described herein, according to at least one example.

Certain embodiments of the present disclosure relate to devices, computer-readable medium, and methods for implementing various heartrate tracking techniques. Examples are described with reference to wearable devices that can detect, collect, process, and/or track various types of different biometric data (e.g., heartrate). The wearable devices may be generally configured to be worn on a wrist, or other location (e.g., chest, ankle, finger, etc.) conducive to collecting heartrate data. The heartrate data may be detected and/or collected by various sensors or sensing devices that can be configured as part of the wearable device or configured to send data to the wearable device. In some instances, the wearable device may be equipped with an infrared (IR) sensor (e.g., an IR light emitting diode (LED) or "IR LED") that is configured to sense a user's heartrate (e.g., through the skin of the user). In some cases, the IR LED may be a less sensitive and/or less accurate sensor of a user's heartrate, at least with respect to some other sensors. For example, a non-IR LED (e.g., a green LED) may be more sensitive and may be capable of being more accurate than the IR LED. As such, the wearable device may be equipped with both an IR LED (e.g., for certain instances) and a non-IR LED (e.g., for other instances). Other sensors can also be used that provide various levels of sensitivity and/or accuracy.

Additionally, in some examples, data artifacts collected by the wearable devices may interfere with accurate tracking of heartrate data. For example, accelerometer data (e.g., collected by an accelerometer or other motion sensor) may be collected by the wearable device while a user is moving (e.g., walking, running, cycling, etc.). However, this accelerometer data may interfere with the heartrate tracking. Additionally, in some examples, movement of the user may make it difficult to accurately collect the heartrate data of the user. For example, while a user is running, the wearable device may be shaken or otherwise knocked around on the user's arm, making it difficult for the heartrate sensors to accurately collect heartrate readings. As such, different heartrate collection, processing, and/or tracking techniques may be useful in different situations. In particular, using these different techniques, when appropriate, enables improved heartrate tracking by filtering out unnecessary artifact data and/or using context-appropriate algorithms to process the heartrate data.

By way of example, the wearable device can be configured detect a type of action of a user (e.g., whether the user is walking, running, using a software application, or the like). For the sake of this disclosure, being sedentary (e.g., no action or activity) is considered an action. Thus, sitting, lying down, etc. can all be actions that are detectable by the wearable device. The wearable device may then determine a context of the action. Contexts can be used to determine appropriate data collection techniques (e.g., which sensors to use), data processing techniques (e.g., which algorithms to use), and/or data tracking techniques (e.g., how to tag or classify the processed data). Once the context is determined, the wearable device can determine how to collect the data and then how to process the data. Once processed, the wearable device can determine how tag the data so that it can be represented in a user interface (UI) in a way that is understandable to a user.

In some embodiments, heartrate data can be collected, processed, and tracked in various ways. Collecting heartrate data generally involves one or more physical sensors of a device sensing heartbeats of a user for a period of time. The collection part can involve tagging or otherwise associating the heartbeat data point with a timestamp or other information that indicates when the heartbeat data point was collected. Over a period of time, multiple heartbeats can be aggregated to calculate a heartrate, which can be defined as the number of heartbeats per minute. Even if the data is not collected for an entire minute, the per-minute heartrate can be calculated. For example, if five heartbeats are sensed in a ten second period, the per-minute heartrate can be calculated by multiplying the five heartbeats by six (e.g., because there are six, ten second periods per minute) to arrive at a heartrate of thirty per minute. Processing the heartrate data can include adding or subtracting heartbeats from the aggregated set of heartbeats over the period and/or running an algorithm on the data to arrive at a different number (e.g., a revised heartrate). Further, in some examples, tracking the heartrate data can include tagging or otherwise associating each collected heartrate or set of heartrates with one or more context indicators (e.g., labels) that can be used to store the heartrate information in an organized fashion. Additionally, in some examples, tracking the heartrate data may also include generating, providing, or displaying a UI that presents the heartrate data with the associated tags (e.g., indicators, labels, etc.).

FIG. 1 is a simplified block diagram illustrating example flow 100 for providing various heartrate tracking techniques as described herein, according to at least one example. In example flow 100, user 102 may be wearing wearable device 104 that is configured to collect biometric information (e.g., a heartrate) of user 102 while wearable device 104 is being worn. In some cases, wearable device 104 can be configured with a plurality of software applications that can each be configured or programmed for various operations. For example, wearable device 104 may have various applications installed therein, such as a breathing application, a workout application, a health application that can aggregate health and/or activity data, etc. Additionally, in some examples, the health application may be part of the operating system of wearable device 104 as opposed to a software application that was individually downloaded and installed by user 102. In other words, the health application may come pre-loaded with wearable device 104 and may not be optional. As described herein, each block of example flow 100 can be performed by the operating system of wearable device 104, a health application that is part of the operating system of wearable device 104, a separate health application or other application, a third-party application being executed by wearable device 104 (e.g., an application that is supported by the operating system of wearable device 104 but is designed and built by another entity), or another computer that is in communication with wearable device 104 (e.g., a mobile device of the user such a smart phone and/or a server computer that is remote from both wearable device 104 and the mobile device).

At block 106, wearable device 104 may detect that a first application of wearable device 104 (e.g., "App 1") is launched. Launching the application may entail selection of the application by user 102 (e.g., via a UI of wearable device 104). Alternatively, the application may be launched in response to a user activity (e.g., a running application may be launched automatically if it is determined that user 102 has started running). The first application (e.g. "App 1") may be configured to perform one or more operations on wearable device 104 and present one or more UIs on the display screen of wearable device 104. In some examples, the first application may be user-configurable, meaning that user 102 can configure the operations and/or the UI as desired.

At block 108, wearable device 104 may receive first criteria input. The first criteria input may include configuration information for configuring the first application. For example, if the first application is a breathing application, user 102 may configure the breathing application for a particular amount of time (e.g., how long user 102 wishes to perform the breathing exercise). In other examples, the first criteria may configure the first application regarding other settings of the first application and/or wearable device 104 in general.

At block 110, wearable device 104 may collect first heartrate metrics over a first period of time (e.g., period 112). As noted, these heartrate metrics may be collected by one or more different physical sensors of wearable device 104. Additionally, the type of sensors used and one or more algorithms used to process the heartrate data may be specific for the first application and the first criteria. In other words, a determination may be made by wearable device 104 as to which sensors to use and with which algorithms to process the heartrate data based at least in part on the first application and the first criteria. Further, these determinations may also be made based at least in part on what the user is doing when (e.g., an activity or lack of activity in which the user is involved).

At block 114, wearable device 104 may track the first heartrate data that is collected at block 110. The first heartrate data may be tagged with metadata or other information that indicates that the first heartrate data collected at block 110 is associated with the first application, with time period 112, and/or with a context that is determined based at least in part on the activity of a user, the first application itself, or any other information that can help determine the context. Additionally, the first heartrate metrics can be tracked by presenting them in chart 116. In some examples, chart 116 can be designed with the x-axis identifying time (e.g., time of day) and the y-axis identifying heartrate (e.g., a per-minute value).

At block 118, wearable device 104 may detect that a second application of wearable device 104 (e.g., "App 2") is launched. Launching the application may entail selection of the second application by user 102 (e.g., via a UI of wearable device 104). Alternatively, the second application may be launched in response to a user activity (e.g., a walking application may be launched automatically if it is determined that user 102 has started walking). The second application (e.g. "App 2") may be configured to perform one or more operations on wearable device 104 and present one or more UIs on the display screen of wearable device 104. In some examples, the second application may be user-configurable, meaning that user 102 can configure the operations and/or the UI as desired. Additionally, the second application may be different from the first application in both name and functionality. For example, the first application may be a breathing application while the second application may be a workout application.

At block 120, wearable device 104 may receive second criteria input. The second criteria input may include configuration information for configuring the second application. For example, if the second application is a workout application, user 102 may configure the workout application for a particular amount of time (e.g., how long user 102 wishes to exercise). In other examples, the second criteria may configure the second application regarding other settings of the second application and/or wearable device 104 in general.

At block 122, wearable device 104 may collect second heartrate metrics over a second period of time (e.g., period 124). As noted, these heartrate metrics may be collected by one or more different physical sensors of wearable device 104. Additionally, the type of sensors used and one or more algorithms used to process the heartrate data may be specific for the second application and the second criteria, and may be different from the type of sensors and/or algorithms used by for the first application. In other words, a determination may be made by wearable device 104 as to which sensors to use and with which algorithms to process the heartrate data based at least in part on the second application and the second criteria. Further, these determinations may also be made based at least in part on what the user is doing when (e.g., an activity or lack of activity in which the user is involved).

At block 124, wearable device 104 may track the second heartrate data that is collected at block 122. The second heartrate data may be tagged with metadata or other information that indicates that the second heartrate data collected at block 122 is associated with the second application, with time period 124, and/or with a context that is determined based at least in part on the activity of a user, the second application itself, or any other information that can help determine the context. Additionally, the second heartrate metrics can be tracked by presenting them in chart 128. In some examples, chart 128 can be designed with the x-axis identifying time (e.g., time of day) and the y-axis identifying heartrate (e.g., a per-minute value).

Figure 2:
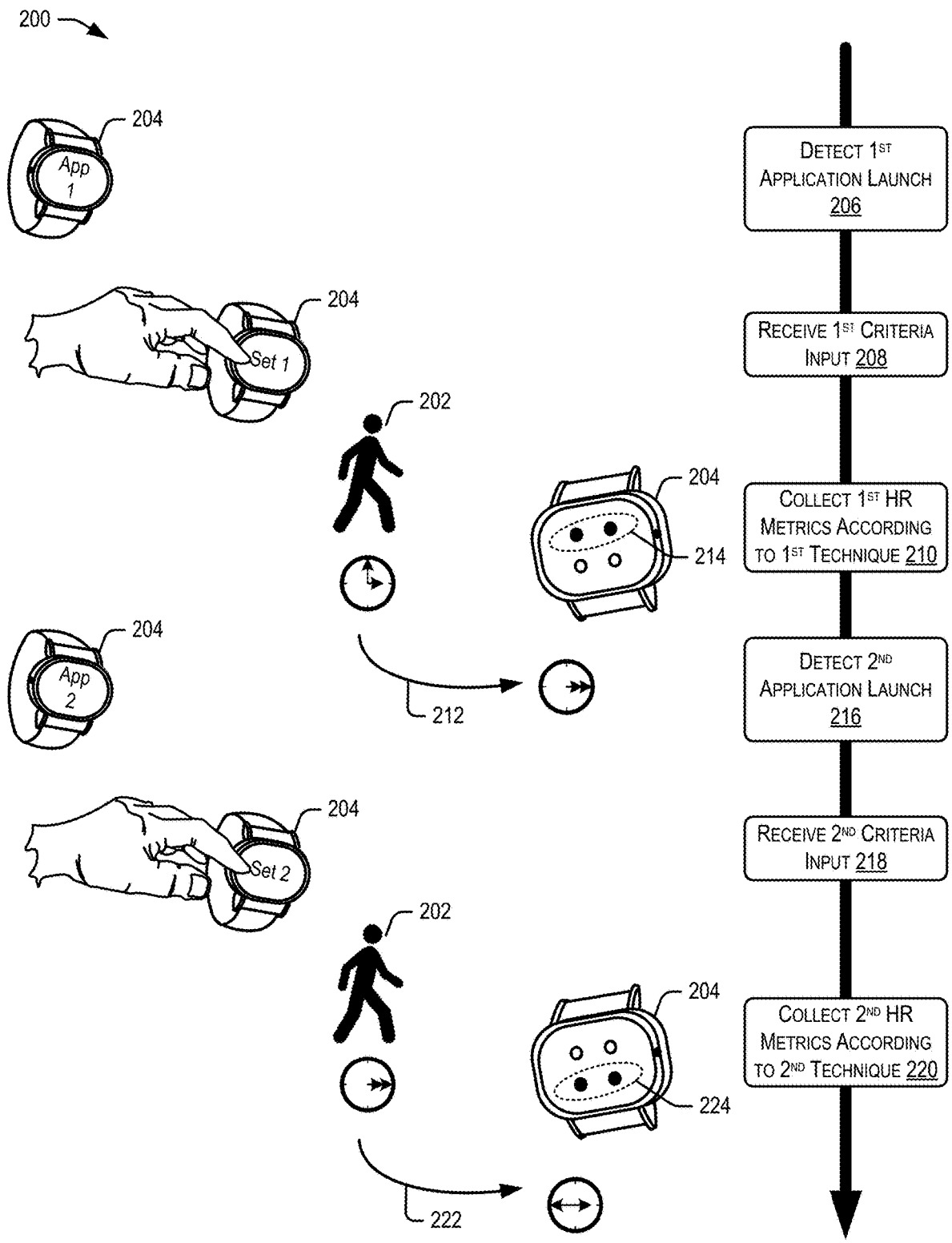
FIG. 2 is another simplified block diagram illustrating another example flow for providing various heartrate tracking techniques as described herein, according to at least one example.

FIG. 2 is another simplified block diagram illustrating example flow 200 for providing various heartrate tracking techniques as described herein, according to at least one example. In example flow 200, user 202 may be wearing wearable device 204 (e.g., which could be the same as wearable device 104) that is configured to collect biometric information (e.g., a heartrate) of user 202 while wearable device 204 is being worn. In some cases, wearable device 204 can be configured with a plurality of software applications that can each be configured or programmed for various operations. For example, wearable device 204 may have various applications installed therein, such as a breathing application, a workout application, a health application that can aggregate health and/or activity data, etc. Additionally, in some examples, the health application may be part of the operating system of wearable device 204 as opposed to a software application that was individually downloaded and installed by user 202. In other words, the health application may come pre-loaded with wearable device 204 and may not be optional. As described herein, each block of example flow 200 can be performed by the operating system of wearable device 204, a health application that is part of the operating system of wearable device 204, a separate health application or other application, a third-party application being executed by wearable device 204 (e.g., an application that is supported by the operating system of wearable device 204 but is designed and built by another entity), or another computer that is in communication with wearable device 204 (e.g., a mobile device of the user such a smart phone and/or a server computer that is remote from both wearable device 204 and the mobile device).

At block 206, wearable device 204 may detect that a first application of wearable device 204 (e.g., "App 1") is launched. Launching the application may entail selection of the application by user 202 (e.g., via a UI of wearable device 204). Alternatively, the application may be launched in response to a user activity (e.g., a breathing application may be launched automatically if it is determined that user 202 desires to perform breathing exercises or if it is determined that it is a good time to recommend breathing exercises to user 202). The first application (e.g. "App 1") may be configured to perform one or more operations on wearable device 204 and present one or more UIs on the display screen of wearable device 204. In some examples, the first application may be user-configurable, meaning that user 202 can configure the operations and/or the UI as desired.

At block 208, wearable device 204 may receive first criteria input. The first criteria input may include configuration information for configuring the first application. For example, if the first application is a breathing application, user 202 may configure the breathing application for a particular amount of time (e.g., how long user 202 wishes to perform the breathing exercise). In other examples, the first criteria may configure the first application regarding other settings of the first application and/or wearable device 204 in general.

At block 210, wearable device 204 may collect first heartrate metrics over a first period of time (e.g., period 212) and according to a first technique. In some examples, collecting the first heartrate metrics according to the first technique may include utilizing first set of LEDs 214. That is, based at least in part on the first application (e.g., a type of the first application) and/or the first criteria received at block 208, wearable device 204 may flash first set of LEDs 214. In some examples, first set of LEDs 214 may be IR LEDs that collect heartrate data at a lower accuracy than other sensors of wearable device 204.

At block 216, wearable device 204 may detect that a second application of wearable device 204 (e.g., "App 2") is launched. Launching the application may entail selection of the second application by user 202 (e.g., via a UI of wearable device 204). Alternatively, the second application may be launched in response to a user activity (e.g., a walking application may be launched automatically if it is determined that user 202 has started walking). The second application (e.g. "App 2") may be configured to perform one or more operations on wearable device 204 and present one or more UIs on the display screen of wearable device 204. In some examples, the second application may be user-configurable, meaning that user 202 can configure the operations and/or the UI as desired. Additionally, the second application may be different from the first application in both name and functionality. For example, the first application may be a breathing application while the second application may be a workout application.

At block 218, wearable device 204 may receive second criteria input. The second criteria input may include configuration information for configuring the second application. For example, if the second application is a workout application, user 202 may configure the workout application for a particular number of repetitions or a target heartrate. In other examples, the second criteria may configure the second application regarding other settings of the second application and/or wearable device 204 in general.

At block 220, wearable device 204 may collect second heartrate metrics over a second period of time (e.g., period 222) and according to a second technique. In some examples, collecting the second heartrate metrics according to the second technique may include utilizing second set of LEDs 224. That is, based at least in part on the second application (e.g., a type of the second application) and/or the second criteria received at block 218, wearable device 204 may flash second set of LEDs 224. In some examples, second set of LEDs 224 may be green LEDs that collect heartrate data at a higher accuracy than other sensors of wearable device 204 (e.g., higher accuracy than IR LEDs 214). In some instances, second set of LEDs 224 may be utilized with the second application (or with some other activity not even associated with an application) because use of the second application or performance of the other activity is more conducive to using the more accurate LEDs (e.g., user of the second application or performance of the other activity are not high activity or high motion events).

Figure 3:
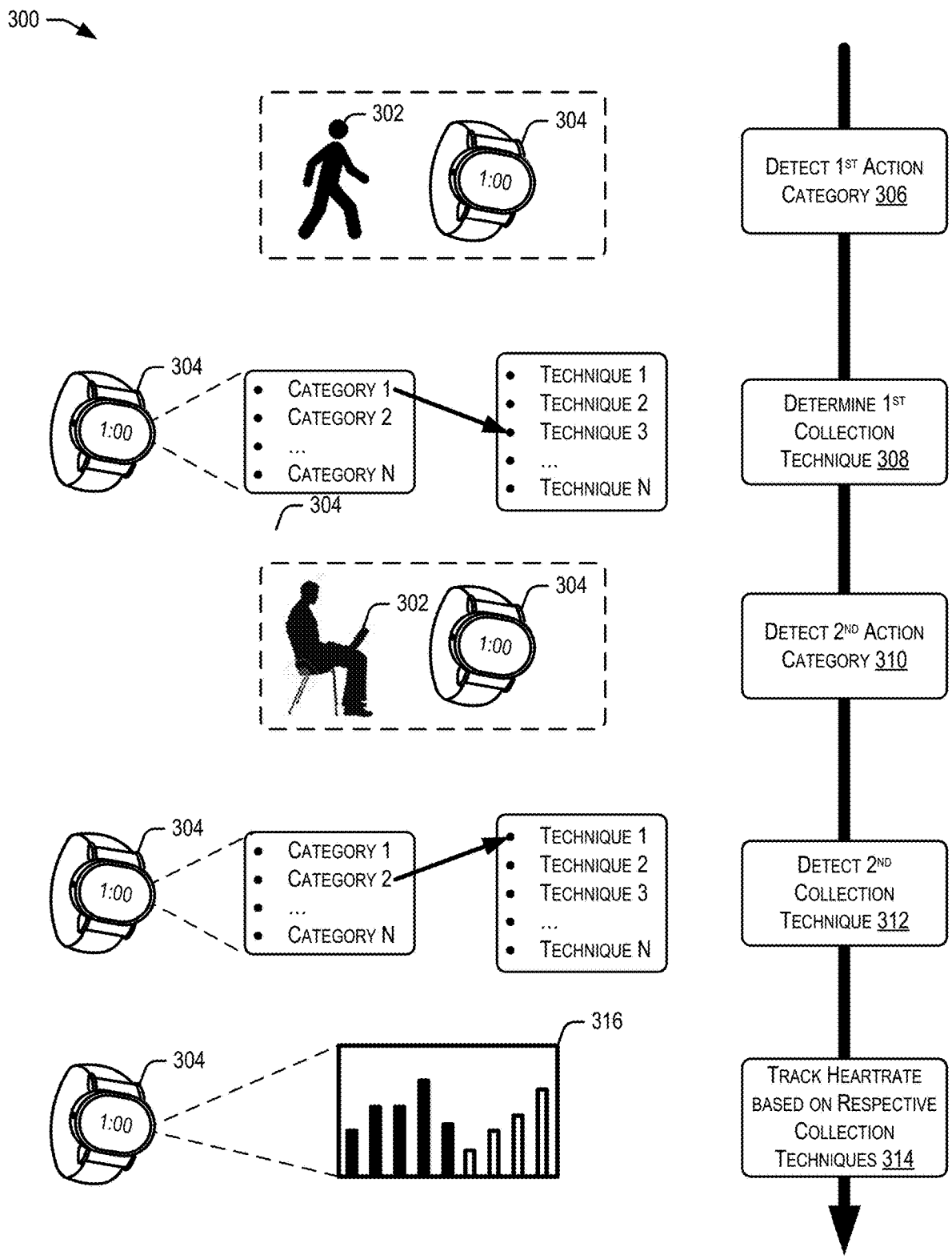
FIG. 3 is another simplified block diagram illustrating another example flow for providing various heartrate tracking techniques as described herein, according to at least one example.

FIG. 3 is another simplified block diagram illustrating example flow 300 for providing various heartrate tracking techniques as described herein, according to at least one example. In example flow 300, user 302 may be wearing wearable device 304 (e.g., which could be the same as wearable device 104 of FIG. 1 and/or wearable device 204 of FIG. 2) that is configured to collect biometric information (e.g., a heartrate) of user 302 while wearable device 304 is being worn. In some cases, wearable device 304 can be configured with a plurality of software applications that can each be configured or programmed for various operations. Additionally, in some examples, wearable device 304 may be configured to collect accelerometer information (e.g., based at least in part on movement of user 302) and determine activity or actions of a user. Activities may include running, walking, cycling, using an elliptical machine, swimming, sitting, resting, sleeping, standing still, performing a breathing exercise. Additionally, in some examples, other sensors (e.g., besides accelerometer sensors) may collect other data that can be used to determine the actions of the user. As described herein, each block of example flow 300 can be performed by the operating system of wearable device 304, a health application that is part of the operating system of wearable device 304, a separate health application or other application, a third-party application being executed by wearable device 304 (e.g., an application that is supported by the operating system of wearable device 304 but is designed and built by another entity), or another computer that is in communication with wearable device 304 (e.g., a mobile device of the user such a smart phone and/or a server computer that is remote from both wearable device 304 and the mobile device).

At block 306, wearable device 304 may detect a first action category associated with user 302 and/or the use of wearable device 304. As noted above, the first action may be determined by information collected by an accelerometer of wearable device 304 and/or a combination of different sensors of wearable device 304. Once the motion and/or other information is collected, wearable device 304 may be able to determine an action category. Action categories can include active (e.g., user 302 is running, walking, working out, etc.), sedentary (e.g., user 302 is resting, sitting, laying down, sleeping, etc.), user-initiated (e.g., user 302 selected and/or launched an application of wearable device 304. Selecting an application can be different from launching an application in that when an application is launched, the application is not currently being executed; however, when an application is selected, it may have already been launched.

At block 308, wearable device 304 may determine a first collection technique for collecting and/or processing heartrate data of user 302. In some cases, a collection technique may be selected or determined based at least in part on the action category detected at block 306. For example, there may be any number of action categories 1-N (e.g., as described above) and any number of collection techniques 1-N. In this example, action category 1 may be detected at block 306, and based at least in part on that detection, wearable device 304 may determine to utilize collection technique 3.

At block 310, wearable device 304 may detect a second action category associated with user 302 and/or the use of wearable device 304. As noted above, the second action may be determined by information collected by an accelerometer of wearable device 304 and/or a combination of different sensors of wearable device 304. Once the motion and/or other information is collected, wearable device 304 may be able to determine an action category. In some examples, the second action category detected at block 306 may be different from the action category detected at block 301. For example, action category 1 was detected at block 306 while action category 2 may be detected at block 310.

At block 312, wearable device 304 may determine a second collection technique for collecting and/or processing heartrate data of user 302. In some cases, the second collection technique may be selected or determined based at least in part on the action category detected at block 310. For example, action category 2 may be detected at block 310, and based at least in part on that detection, wearable device 304 may determine to utilize collection technique 1. However, any other mapping of category to technique may be utilized, as desired, and any number of categories as well as techniques may exist.

At block 314, wearable device 304 may track the heartrate of user 302 based at least in part on respective collection techniques. For example, first heartrate data may be collected according to technique 3 for a first period of time and/or while user 302 is performing an activity that corresponds to action category 1. Additionally, second heartrate data may be collected according to technique 1 for a second period of time and/or while user 302 is performing an activity that corresponds to action category 2. The first heartrate data may be tagged with metadata or other information that indicates that the first heartrate data collected according to technique 3 is associated with a first time, with the first category, and/or with a first context. Additionally, the second heartrate data may be tagged with metadata or other information that indicates that the second heartrate data collected according to technique 1 is associated with a second time, with the second category, and/or with a second context. Additionally, the first heartrate metrics and the second heartrate metrics can be tracked by presenting them in chart 316. In some examples, chart 116 can be designed with the x-axis identifying time (e.g., time of day) and the y-axis identifying heartrate (e.g., a per-minute value). Different data points in chart 316 may be color-coded to represent respective action categories.

Figure 4:
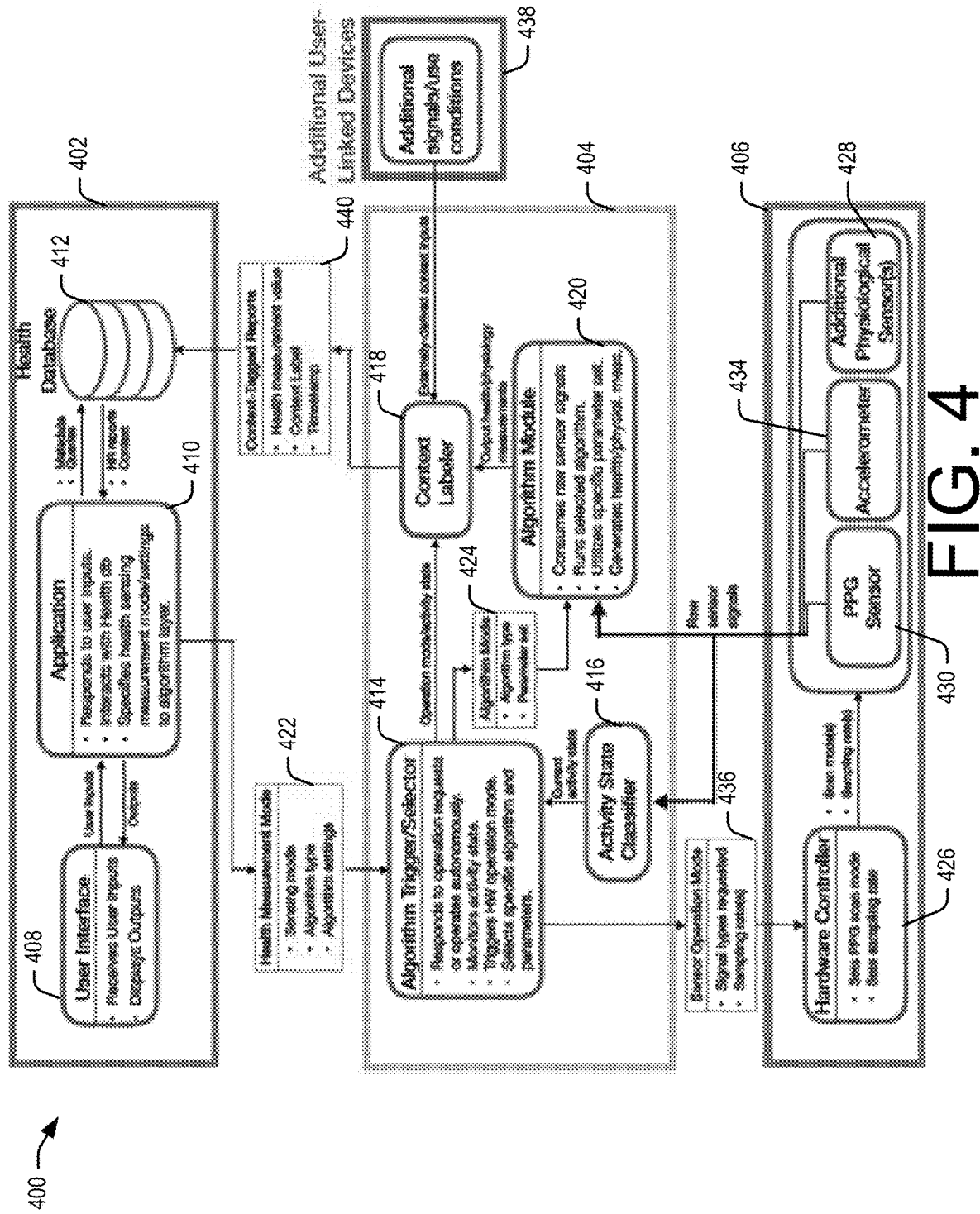
FIG. 4 is a simplified block diagram illustrating an example architecture for providing various heartrate tracking techniques as described herein, according to at least one example.

FIG. 4 is another simplified block diagram illustrating example architecture 400 for implementing various heartrate tracking techniques as described herein. In some examples, architecture 400 may include application layer 402, algorithm layer 404, and sensor/hardware layer 406. Some or all of these layers may be executed or otherwise implemented by a wearable device such as wearable devices 104, 204, 304 of FIGS. 1, 2, 3, respectively. However, in some examples, any or all of the different layers may be implemented on various other devices. For example, application layer 402 and sensor/hardware layer 406 may implemented by a wearable device, while algorithm layer 404 may be executed by another mobile device of a user or by a server computer.

In some embodiments, application layer 402 may be configured with user interface 408, one or more applications 410, and a database (e.g., health database 412). User interface 408 can receive user inputs and transmit them to application 410. User interface 408 may also be configured to present/display out to the user. The outputs may be received by application 410 and may include charts (e.g., like chart 98 of FIG. 1 or chart 316 of FIG. 3) or other information for the user. Application 410 may be configured to respond to user inputs, interact with health database 412, and/or specify health sensing measurement mode/settings to algorithm layer 404. Application 410 may also make queries to health database 412 and/or store/receive metadata to/from health database 412.

Algorithm layer 404 may be configured with algorithm trigger/selector 414, activity state classifier 416, context labeler 418, and algorithm module 420. In some examples, application 410 may be configured to communicate with algorithm trigger/selector 414 of algorithm layer 404 by providing health measurement mode information 422. Health measurement mode information 422 may include sensing mode, algorithm type, and/or algorithm settings which can help algorithm trigger/selector 414 determine the appropriate heartrate tracking technique to be used.

In some cases, algorithm trigger/selector 414 is configured to respond to operation requests or operates autonomously. For example, if a user launches an application (e.g., a workout application) or starts a workout, algorithm trigger/selector 414 can respond to that operation request by selecting an appropriate tracking technique. However, in other examples, it may act autonomously to select a tracking technique based at least in part on a user's inaction or an activity detected by activity state classifier 416. Additionally, algorithm trigger/selector 414 may be configured to monitor activity state (e.g., in order to determine an activity/action of the user), trigger hardware operation modes, and/or select specific algorithms and parameters for performing each tracking technique.

Algorithm trigger/selector 414 may provide algorithm mode information 424 (e.g., including algorithm type and parameter sets for implementing the algorithms) to algorithm module 420. Algorithm module 420 may be configured to consume raw sensor signals (e.g., heartrate data), run selected algorithms, utilize specific parameter sets, and generate health/physiological measurements.

Sensor/hardware layer 406 may include hardware controller 426 and one or more sensors 428 (e.g., heartrate sensors 430, accelerometers 432, and/or other sensors 434). Heartrate sensors 430 may include IR LEDs and/or green LEDs or other (more sensitive) sensors for collecting heartrate metrics). In some examples, algorithm trigger/selector 414 of algorithm layer 404 can provide sensor operation mode information 436 to hardware controller 426. Sensor operation mode information 436 can include signal types requested and/or sampling rates that are determined by algorithm trigger/selector 414. Once this information is received by hardware controller 426, hardware controller 426 can set PPG scan modes and sampling rates of sensors 428 (e.g., green LEDs and/or IR LEDs). Hardware controller 426 can then control sensors 428 regarding scan modes and sampling rates so that sensors 428 (in particular, the LEDs that collect heartrate data) can operate according to the determined tracking technique.

Raw signal data can be collected by sensors 428 and passed to activity state classifier 416 in order to aid in determining an activity or state of the user. Current activity state can be regularly determined (classified) by activity state classifier 416 and fed back to algorithm trigger/selector 414 for regular determinations of what signal types and sampling rates should be provided to hardware controller 426. Additionally, the raw signal data can be provided the algorithm module 420 for consumption. Algorithm module 420 can consume the raw signal (sensor) data, run selected algorithms on the raw data, utilize specific parameter sets of the raw data, and generate health/physiological measurements (as described above) based at least in part on the raw signal data. The health/physiological measurements can be provided to context labeler 418.

In some examples, context labeler 418 can receive operation mode/activity state information from algorithm trigger/selector 414, the health/physiological measurements from algorithm module 420, and externally-derived context inputs from additional devices 438. Context labeler 418 can use all of this information to appropriately label the label with a context and provide context-tagged reports 440 to health database 412. Reports 440 can include health measurement values, context labels, and/or timestamps. When application 410 requests heartrate reports and context information, health database 412 is able to provide such information based at least in part on reports 440 from context labeler 418. Application 410 can then transmit this information as an output to user interface 408 for display.

In some examples, a workout app (or any application, e.g., application 410) can call an application programming interface (API) of a health application or operating system implementation in order to indicate that a workout is started. Calling this API may signal algorithm trigger/selector 414 to instruct hardware controller 426 and/or algorithm module 420. Additionally, third-party applications may similarly make the same API call. There may also be other (e.g., workout-specific) APIs for indicating a run, walk, or cycling working is beginning. In this way, algorithm trigger/selector 414 may be instructed regarding exactly which tracking technique to use. It may also be possible for a user to initiate a tracking technique without specifically selecting or launching an application (e.g., by voice activation, gestures, or the like).

In some embodiments, certain applications (e.g., application 410 or the like) may be associated with different algorithms. For example, algorithm trigger/selector 414 may select different algorithms for different types of workouts that are part of the same workout application. Examples include using different algorithms and/or sensors for running versus walking, versus using an elliptical machine, versus cycling. As noted, both accelerometer data and heartrate data may be received; however, some of the accelerometer data be filtered out to avoid data artifacts interfering with the heartrate data.

Heartrate collection and processing may be different for each determined context. Additionally, different operating modes may be associated with different groups of contexts. Contexts can include workout, streaming, breathing, background, sedentary, walking, and wheelchair in motion. For the workout context, the following operating mode details apply:

Algorithm module 420 will receive a stream of continuous heartrate output until a workout is ended by the user.

High-frequency LEDs (e.g., green LEDs) and accelerometer signals are used.

Motion-tolerant, frequency-domain algorithm (parameters are specific to the workout type) are used.

For the streaming context (e.g., a user initiated spot check of heartrate data), the following operating mode details apply:

Initial heartrate data is produced and output every few seconds (e.g., every five seconds), and can continue until the display of the wearable device sleeps (e.g., up to sixty seconds).

High-frequency LEDs and 3-axis accelerometer signals are used.

Time+frequency-domain heartrate algorithms are used.

For the breath context, the following operating mode details apply:

While a user remains stationary, one high-precision heartrate per minute can be reported.

High-frequency LEDs and 3-axis accelerometer signals are used.

Time-domain heartrate algorithms are used.

For the background context (e.g., autonomous mode), the following operating mode details apply:

A user's activity state and gross motion levels can be continuously monitored.

Low-power sensing mode (e.g., low-frequency IR LEDs) and time-domain heartrate algorithms are used unless and/or until a walking state is detected.

An at-rest status can be reported during quiescent periods (e.g., several minutes with no gross motion).

Walking-specific heartrate algorithms can be triggered (e.g., using high-frequency green LEDs and accelerometer signals) if walking state is detected for sufficient duration.

Regarding labeling by context labeler 418, the workout context label can be used when heartrate reports are generated while using the workout application and the streaming context label can be used when heartrate reports are generated while using the heartrate application (e.g., spot check), or during post-workout recovery period. Additionally, the breath context label can be used when heartrate reports are generated while using the breathing app. The background context label can be used when heartrate reports are produced from continuous background monitoring, when recent activity does not indicate an at-rest state; however, the sedentary context label can be used when heartrate reports are generated from continuous background monitoring, when recent activity indicates an at-rest state. In some examples, the walking context label can be used when heartrate reports are generated during background mode operation when a walking state has been detected, and the wheelchair context label can be used when heartrate reports are generated during background mode operation for wheelchair users when a motion state has been detected.

In some instances, different context-derived heartrate reports can be generated in different scenarios. For example, for resting heartrate reports, a summary report of heartrate values having sedentary context can be provided. Additionally, a user's physiological baseline resting heartrate, using intraday measurements can be estimated. Further, this can be updated throughout the day and stored in health database 412 at the end of the day. For resting heartrate reports, on the other hand, a summary report of heartrate values having a walking context can be provided. A user's typical heartrate during non-exercise walking can be estimated. This can also be updated throughout the day and stored in health database 412 at the end of the day.

Figure 5:
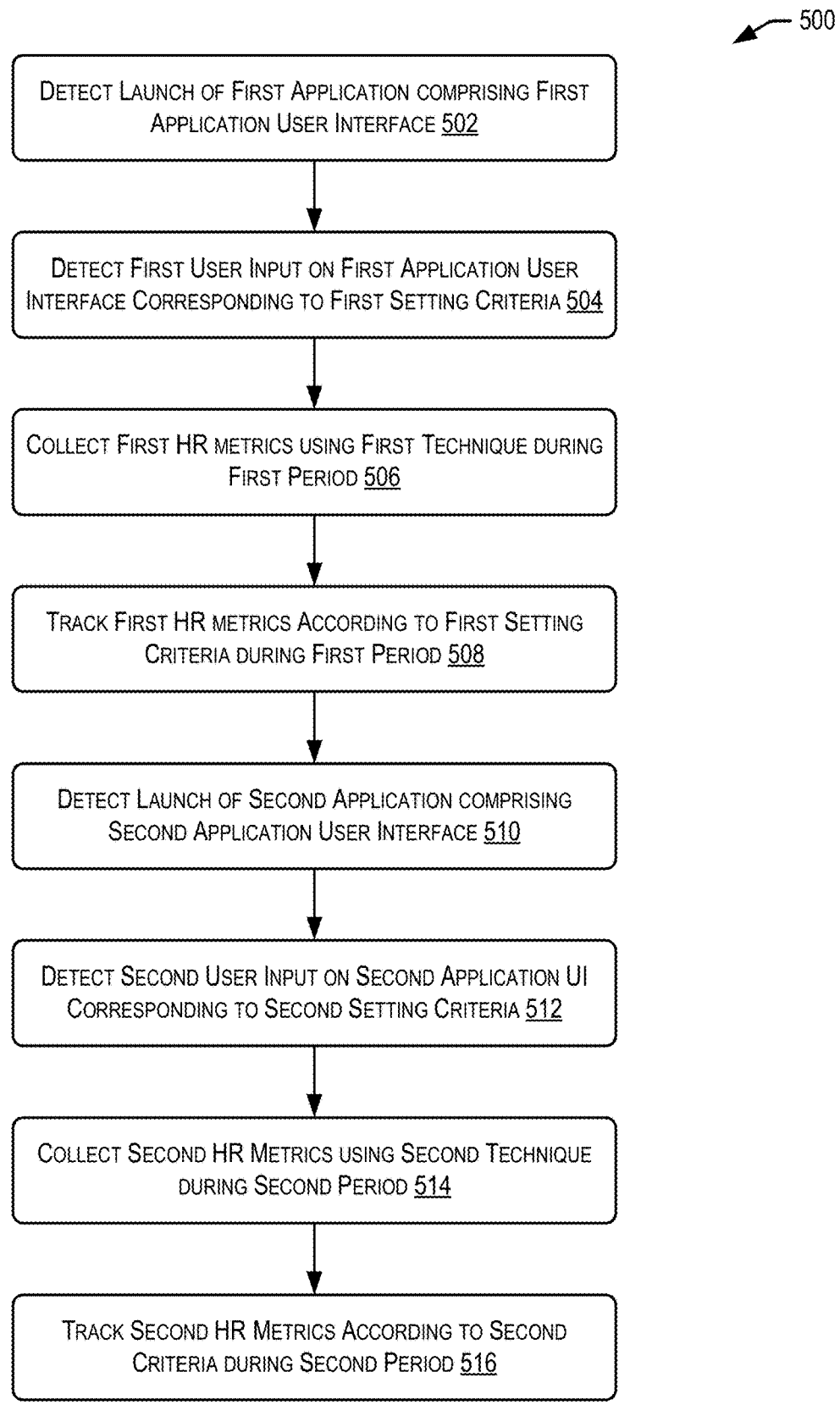
FIG. 5 is a simplified flowchart of an example method for providing various heartrate tracking techniques as described herein, according to at least one example.

FIG. 5 illustrates an example flow diagram showing process 500 for implementing various heartrate tracking techniques, according to at least a few embodiments. In some examples, the wearable device 104 of FIG. 1 (e.g., utilizing at least application layer 402, algorithm layer 404, and/or sensor/hardware layer 406 of FIG. 4) may perform the process 500 of FIG. 5.

At block 502, wearable device 104 may detect the launching of a first application comprising a first application user interface. The first application user interface may present configuration settings and/or options for configuring the first application. For example, a user may be able to select an amount of time for performing an activity that the first application can track. Additionally, other parameters may be configured that are appropriate to the first application.

At block 504, wearable device 104 may detect a first user input on the first application user interface corresponding to the first setting criteria. The first setting criteria can correspond to the configuration information noted above with respect to block 502. For example, the first setting criteria might indicate the amount of time for a workout or other activity associated with the first application.

At block 506, wearable device 104 may collect first heartrate metrics using a first heartrate tracking (e.g., collecting and processing) technique during a first period. The first period may correspond to the time included in the configuration information. For example, if the user selected a workout application and configured it for a thirty minute workout, the first period may be for thirty minutes. Additionally, the first heartrate tracking technique may correspond to one or more of the operating modes described above.

At block 508, wearable device 104 may track first heartrate metrics according to the first setting criteria during the first period. As noted, tracking the first heartrate metrics may include labeling the first heartrate metrics according to the heartrate context labels identified above. Additionally, tracking the first heartrate metrics may also include storing the labeled data and providing it in one or more UIs (e.g., in a chart, graph, or the like).

At block 510, wearable device 104 may detect the launching of a second application comprising a second application user interface. The second application user interface may present configuration settings and/or options for configuring the second application. For example, a user may be able to select an amount of time for performing an activity that the second application can track. Additionally, other parameters may be configured that are appropriate to the first application. The second application may be different from the first application and may include different (or the same) configurations or options.

At block 512, wearable device 104 may detect a second user input on the second application user interface corresponding to the second setting criteria. The second setting criteria can correspond to the configuration information noted above with respect to block 510. For example, the second setting criteria might indicate the amount of time for a breathing exercise or other activity associated with the second application.

At block 514, wearable device 104 may collect second heartrate metrics using a second heartrate tracking (e.g., collecting and processing) technique during a second period. The second heartrate tracking technique may correspond to one or more of the operating modes described above, but may be different from the first heartrate tracking technique.

At block 516, wearable device 104 may track second heartrate metrics according to the second setting criteria during the second period. As noted, tracking the second heartrate metrics may include labeling the second heartrate metrics according to the heartrate context labels identified above. Additionally, tracking the second heartrate metrics may also include storing the labeled data and providing it in one or more UIs (e.g., in a chart, graph, or the like).

Embodiments described herein may take the form of, be incorporated in, or operate with a suitable electronic device. One example of such a device is device 600 shown in FIG. 6 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative embodiments of suitable electronic devices include a mobile phone, a tablet computing device, a portable media player, and so on. Still other suitable electronic devices may include laptop/notebook computers, personal digital assistants, touch screens, input-sensitive pads or surfaces, and so on.

Figure 6:
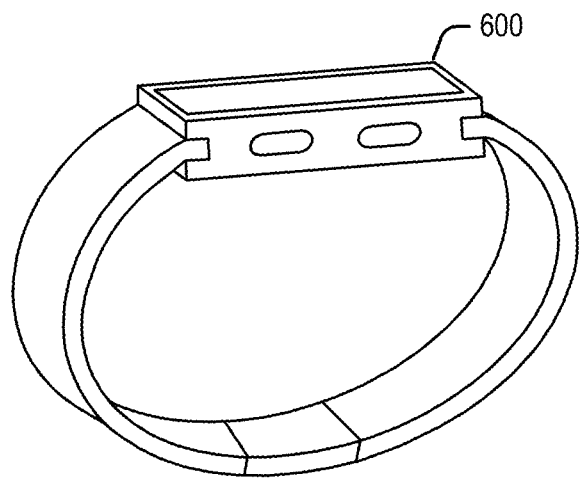
FIG. 6 is a simplified block diagram illustrating example devices for providing various heartrate tracking techniques as described herein, according to at least one example.
Figure 7:
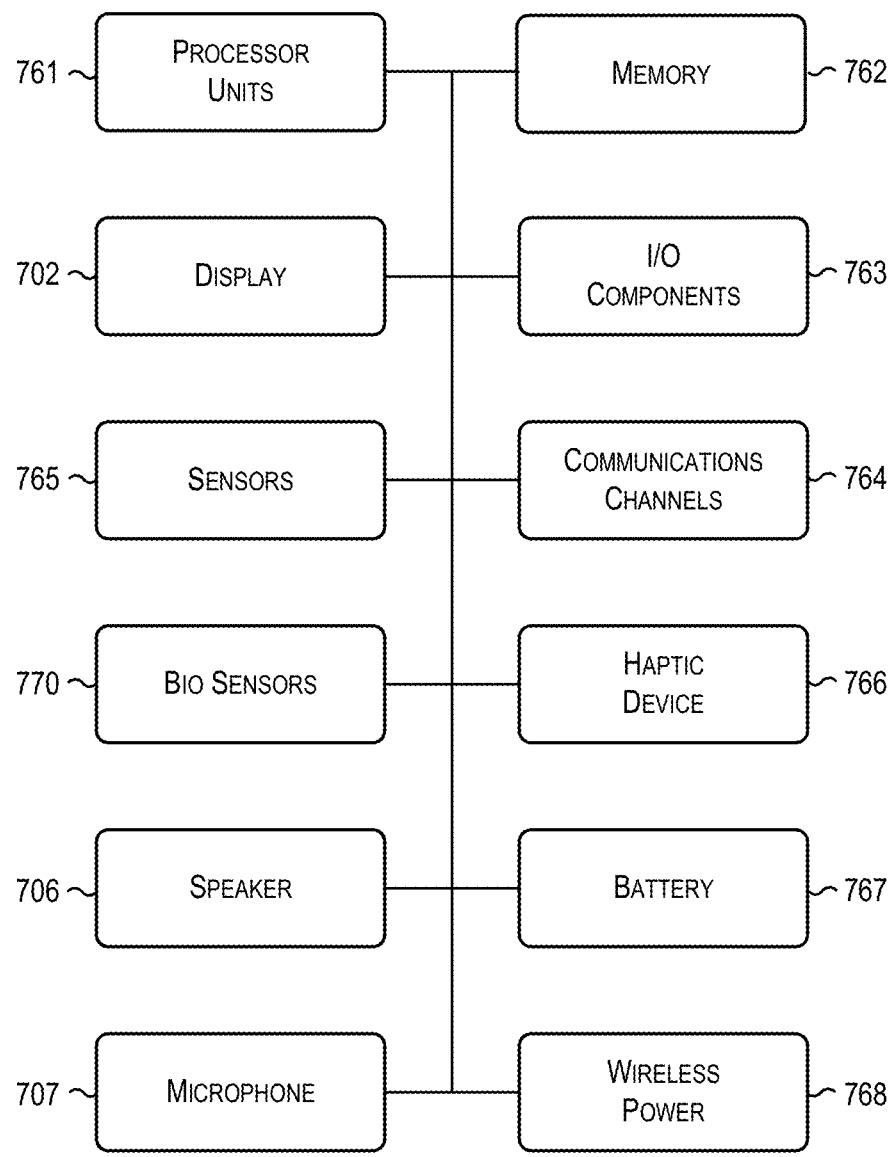
FIG. 7 is a simplified block diagram illustrating another example architecture for providing various heartrate tracking techniques as described herein, according to at least one example.

FIG. 7 depicts an example schematic diagram of wearable electronic device 700 (e.g., similar to device 600 of FIG. 6). As shown in FIG. 7, device 700 includes one or more processing units 761 that are configured to access memory 762 having instructions stored thereon. The instructions or computer programs may be configured to perform one or more of the operations or functions described with respect to device 700. For example, the instructions may be configured to control or coordinate the operation of the various components of the device. Such components include, but are not limited to, display 702, one or more input/output components 763, one or more communication channels 764, one or more sensors 765, speaker 706, microphone 707, and/or one or more haptic feedback devices 766. In some embodiments the speaker and microphone may be combined into a single unit and/or may share a common port through a housing of the device.

Processing units 761 of FIG. 7 may be implemented as any electronic device capable of processing, receiving, or transmitting data or instructions. For example, processing units 761 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

In some embodiments the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some embodiments, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such embodiments the band may include electrical interconnections that permit the two devices to transmit signals to one another and thereby interact with one another.

In many embodiments, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some embodiments.

Device 700 also may comprise one or more touch sensors to determine a location of a touch on the cover glass. A touch sensor may be incorporated into or on the display stack in order to determine a location of a touch. The touch sensor may be self-capacitive in certain embodiments, mutual-capacitive in others, or a combination thereof.

Similarly, device 700 may include a force sensor to determine an amount of force applied to the cover glass. The force sensor may be a capacitive sensor in some embodiments and a strain sensor in other embodiments. In either embodiment, the force sensor is generally transparent and made form transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one embodiment the force sensor may take the form of a gasket extending beneath the periphery of the display. The gasket may be segmented or unitary, depending on the embodiment.

Electronic device 700 may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative embodiments the haptic actuator may be rotary or any other type). A speaker may provide auditory components of an alert and the aforementioned display may provide visual alert components. In some embodiments a dedicated light, display, or other visual output component may be used as part of an alert.

The auditory, haptic and/or visual components of the alert may be synchronized to provide an overall experience to a user. One or more components may be delayed relative to other components to create a desired synchronization between them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output but at a weak or even subliminal level, thereby priming the wearer to receive the auditory output.

Example electronic device 700 may communicate with other electronic devices either through a wired connection or wirelessly. Data may be passed between devices, permitting one device to relay information to another; control another; employ another's sensors, outputs, and/or inputs; and so on.

Figure 8:
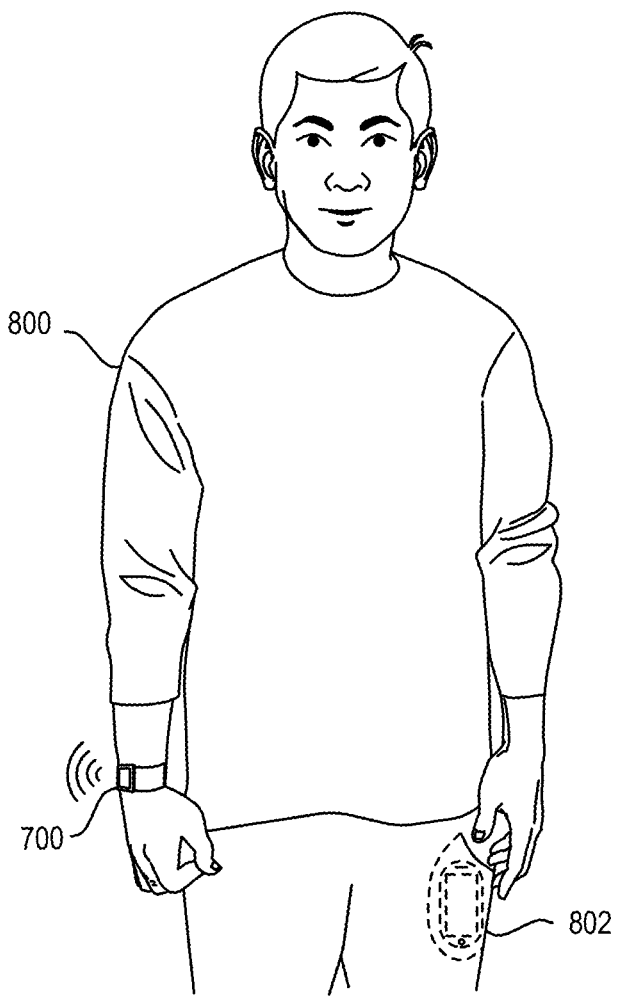
FIG. 8 is a simplified block diagram illustrating additional example devices for providing various heartrate tracking techniques as described herein, according to at least one example.

FIG. 8 depicts user 800 wearing a sample wearable electronic device 700 with a second (e.g., portable) electronic device 802 in his pocket. Data may be wirelessly transmitted between the electronic devices 700, 802, thereby permitting the user 800 to receive, view, and interact with data from the second device 802 by means of the first electronic device 700. Thus, the user 800 may have access to part or all of the second device's functionality through the first electronic device 700 without actually needing to interact directly with the second device 802.

Further, the electronic devices 700, 802 may cooperate not only to share data but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access and the like between the two and ultimately to a user. As one non-limiting example, the electronic device 700 may be unable to place or receive telephone calls while the second device 802 may be able to do so. A user may nonetheless make and/or receive calls through the first device 700, which may employ the second device 802 to actually place or accept a call.

As another non-limiting example, an electronic device 700 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain embodiments may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health information to be provided to a user. In some examples, the sensed biometric information may be used by the alert manager, in part, for managing the electronic content and/or the incoming alerts.

Certain embodiments may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems also may be used (e.g., near field magnetic resonance and radio frequency). Alternatively, the device also may employ wired charging through electrodes.

In certain embodiments, the device may include a rotary input, which may take the form of a crown with a stem. The crown and stem may be rotated to provide the rotary input. Rotation of the stem and/or crown may be sensed optically, electrically, magnetically, or mechanically. Further, in some embodiments the crown and stem may also move laterally, thereby providing a second type of input to the device.

The electronic device may likewise include one or more buttons. The button(s) may be depressed to provide yet another input to the device. In various embodiments, the button may be a dome switch, rocker switch, electrical contact, magnetic switch, and so on. In some embodiments the button may be waterproof or otherwise sealed against the environment.

Various embodiments may include or otherwise incorporate one or more motion sensors. A motion sensor may detect motion of the device and provide, modify, cease, or otherwise affect a state, output, or input of the device or associated applications based on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some embodiments may use a GPS sensor to facilitate or enable location and/or navigation assistance.

As shown in FIG. 7, device 700 may also include one or more acoustic elements, including speaker 706 and/or microphone 707. Speaker 706 may include drive electronics or circuitry and may be configured to produce an audible sound or acoustic signal in response to a command or input. Similarly, microphone 707 may also include drive electronics or circuitry and is configured to receive an audible sound or acoustic signal in response to a command or input. Speaker 706 and microphone 707 may be acoustically coupled to port or opening in the case that allows acoustic energy to pass, but may prevent the ingress of liquid and other debris.

Certain embodiments may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

In certain embodiments, an electronic device may include one or more haptic modules for providing haptic feedback to the user. The embodiments described herein may relate to or take the form of one or more haptic actuators suitable to provide perceivable haptic feedback. Such actuators may include an electromagnetic coil, a permanent magnet or other magnetic field source. The magnetic field may induce motion in a mass of the haptic actuator by exerting a Lorentz force on the mass when the coil is energized. A direction of current through the coil determines the direction of motion of the mass, while the strength of the magnetic field determines the velocity of the mass and thus the magnitude of the haptic output.

In general, haptic actuators implemented in some embodiments may be configured to maximize or enhance resultant mechanical energy, given a very compact form factor of the electronic device.

In one embodiment, the haptic actuator may have a mass at least partially disposed within the coil when the mass is in a rest state. This mass may include two magnets of opposing polarities implemented as a magnet array affixed within a frame; the frame may provide extra weight to the mass and thus a stronger haptic output may be generated. A shaft may extend through the mass such that the mass may freely slide on the shaft.

The magnet array may generate a radial magnetic field that interacts with the magnetic field of the coil when the coil is energized by a current. The Lorentz force resulting from the interaction of the magnetic fields causes the mass to move along a shaft in a first direction. Reversing current flow through the coil reverses the Lorentz force. As a result, the magnetic field or force on the central magnet array is also reversed and the mass may move in a second direction. Thus, mass may move in both directions along the shaft, depending on the direction of current flow through the coil. Passing an alternating current through the coil may cause the central magnet array to move back and forth along a shaft.

In order to prevent the central magnet array from being attracted to the shaft, which could increase friction between the two and thereby increase the force necessary to move the central magnet array and frame, the shaft may be formed from a non-ferritic material such as tungsten, titanium, stainless steel, or the like.

The actuator also may have structures that provide restoring force to the mass. For example, a spring may be located at either end of the shaft. As the mass impacts the spring, the spring compresses and stores kinetic energy. This kinetic energy may be released to return the mass along the shaft, thereby sending it to or near its initial starting position. The kinetic energy in the spring(s) may cooperate with the coil to move the magnet in such a fashion.

Figure 9:
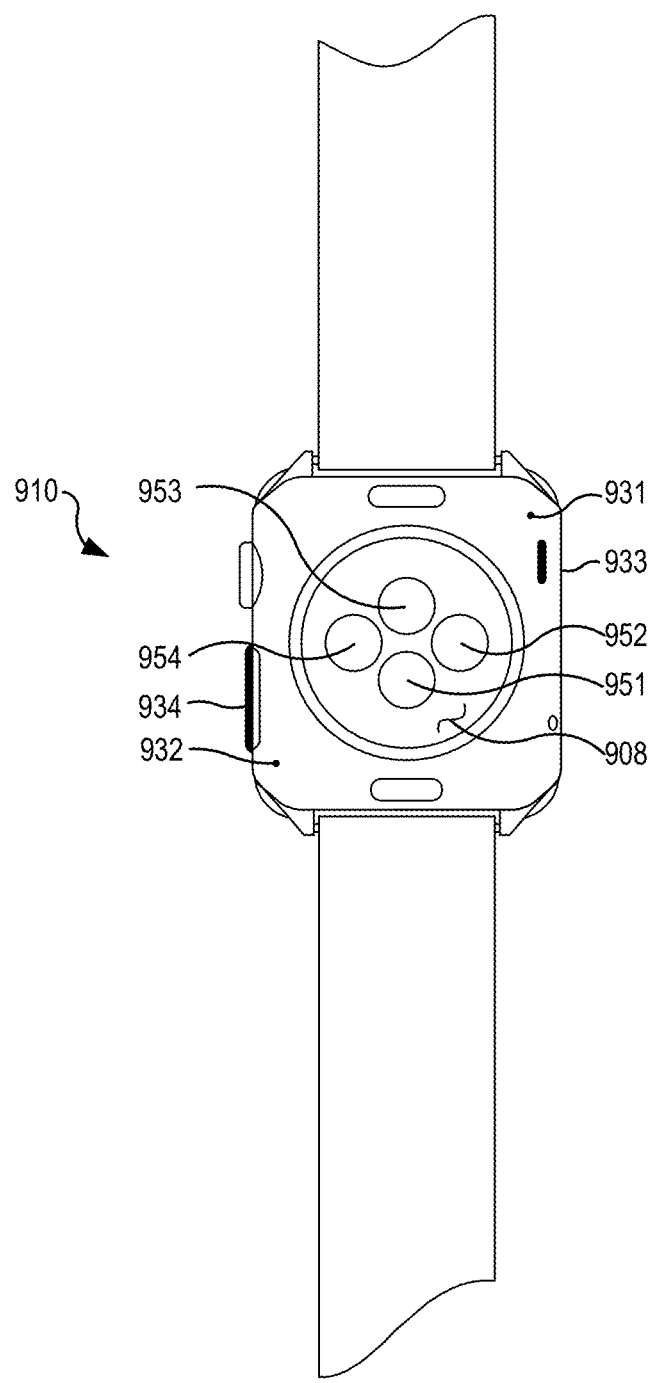
FIG. 9 is a simplified block diagram illustrating additional example devices for providing various heartrate tracking techniques as described herein, according to at least one example.

FIG. 9 depicts an example electronic device 900 having one or more biometric sensors. The electronic device 900 is an example of the wearable user device 106. As shown in FIG. 9, an array of light sources and a photodetector 954 may be disposed on the rear surface of the device 900. In one example, the light sources 951-953 are formed from light emitting diode (LED) elements that are configured to emit light into a portion of the wearer's body (e.g., wrist). The photodetector 954 is shared between the multiple light sources 951-953 and is configured to receive light reflected from the body. The photodetector may be formed from a photodiode material that is configured to produce a signal based at least in part on the received light. In one implementation, the signal produced by the photodetector 954 is used to compute a health metric associated with the wearer. In some cases, the light sources 951-953 and the photodetector 954 form a photoplethysmography (PPG) sensor. The first light source 951 may include, for example, a green LED, which may be adapted for detecting blood perfusion in the body of the wearer. The second light source 952 may include, for example, an infrared LED, which may be adapted to detect changes in water content or other properties of the body. The third 953 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 951-953 and the photodetector 954 may also be used for optical data transfer with a base or other device. While FIG. 9 depicts one example, the number of light sources and/or photodetectors may vary in different examples. For example, another example may use more than one photodetector. Another example may also use fewer or more light sources than are depicted in the example of FIG. 9.

Also as shown in FIG. 9, the device 900 includes multiple electrodes 931, 932, 933, 934 that are located on or near external surfaces of the device 900. In the present example, the device 900 includes a first electrode 931 and a second electrode 932 that are located on or proximate to a rear-facing surface of the device body 910. In this example, the first electrode 931 and the second electrode 932 are configured to make electrical contact with the skin of the user wearing the device 900. In some cases, the first 931 and second 932 electrodes are used to take an electrical measurement or receive an electrical signal from the body of the user. As also shown in FIG. 9, the device 900 may include a third electrode 933 and a fourth electrode 934 that are located on or proximate to a perimeter of the case of the device body 910. In the present example, the third 933 and fourth 934 electrodes are configured to be contacted by one or more fingers of the user who is wearing or interacting with the device 900. In some cases, the third 933 and fourth 934 electrodes are also used to take an electrical measurement or receive an electrical signal from the body of the user. In some cases, the first 931, second 932, third 933, and fourth 934 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 9, the electronic device 900 includes one or more apertures in the case 910. A light source 951-953 may be disposed in each aperture. In one example, each light source 951-953 is implemented as a light-emitting diode (LED). In the present example, the four apertures, three light sources 951-953, and a single detector 954 are used to form one or more sensors. Other examples can include any number of light sources. For example, two light sources can be used in some examples.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one example, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

Although a linear actuator has been described herein, it should be appreciated that other types of actuators may be used in different embodiments. For example, some embodiments may employ a rotary actuator, a piezoelectric actuator, or any other suitable linear or non-linear actuator. Likewise, certain embodiments may employ multiple actuators working in concert.

Illustrative methods and systems for providing various heartrate tracking techniques are described above. Some or all of these systems and methods may, but need not, be implemented at least partially by architectures such as those shown at least in FIGS. 1-8 above. While many of the embodiments are described above with reference to heartrate metrics, it should be understood that any type of biometric information may be collected, processed, and tracked using these techniques. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a network server, the network server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen or keypad), and at least one output device (e.g., a display device, printer or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable storage media for containing code, or portions of code, can include any appropriate media known or used in the art such as, but not limited to, volatile and non-volatile, removable and non-removable media implemented in any method or technology for storage of information such as computer-readable instructions, data structures, program modules or other data, including RAM, ROM, Electrically Erasable Programmable Read-Only Memory (EEPROM), flash memory or other memory technology, CD-ROM, DVD or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments. However, computer-readable storage media does not include transitory media such as carrier waves or the like.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. Additionally, conjunctive language such as the phrase "at least one of X, Y, and Z," unless specifically stated otherwise, should also be understood to mean X, Y, Z, or any combination thereof, including "X, Y, and/or Z."

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A wearable device, comprising:
a user interface;
one or more memories configured to store computer-executable instructions;
a plurality of sensors configured to sense biometric data of a user;
one or more processors in communication with the one or more memories and the plurality of sensors, the one or more processors configured to execute the computer-executable instructions to at least:
track a first action of the user wearing the wearable device using a first sensor of the plurality of sensors;
track a second action of the user using a second sensor of the plurality of sensors;
determine whether a user input is received on the user interface to launch an application of the wearable device;
determine an action category of the user based at least in part on the first action, the second action, and whether the user input to launch the application has been received;
collect heartrate data of the user;
categorize the heartrate data into a heartrate data category based at least in part on the determined action category; and
presenting, via the user interface, heartrate information corresponding to the heartrate data category.

2. The wearable device of claim 1, wherein the heartrate data of the user is collected based at least in part on the determined action category.

3. The wearable device of claim 1, wherein the heartrate data of the user is categorized as sedentary when the first action of the user is below a threshold and the user input to launch the application has not been received.

4. The wearable device of claim 1, wherein the heartrate data of the user is categorized as a breathing category when the user input to launch the application has been received and the application comprises breathing instructions for the user.

5. The wearable device of claim 1, wherein the heartrate data of the user is categorized as workout when the user input to launch the application has been received and the application is configured to track the second action of the user.

6. The wearable device of claim 1, wherein the first sensor is distinct from the second sensor.

7. The wearable device of claim 1, wherein the action category is associated with a particular collection technique, and wherein collecting the heartrate data of the user comprises collecting the heartrate data of the user using the particular collection technique.

8. A computer-implemented method, comprising:
tracking a first action of a user wearing a wearable device using a first sensor of a plurality of sensors of the wearable device;
tracking a second action of the user using a second sensor of the plurality of sensors of the wearable device;

determining, on a user interface of the wearable device, whether a user input is received to launch an application of the wearable device has been launched;

determining an action category of the user based at least in part on the first action, the second action, and whether the user input to launch the application has been received;

collecting heartrate data of the user;

categorizing the heartrate data into a heartrate data category based at least in part on the determined action category; and presenting, via the user interface, heartrate information corresponding to the categorized heartrate data.

9. The computer-implemented method of claim 8, wherein the heartrate data of the user is collected based at least in part on the determined action category.

10. The computer-implemented method of claim 8, wherein the heartrate data of the user is categorized as sedentary when the first action of the user is below a threshold and the user input to launch the application has not been received.

11. The computer-implemented method of claim 8, wherein the heartrate data of the user is categorized as a breathing category when the user input to launch the application has been received and the application comprises breathing instructions for the user.

12. The computer-implemented method of claim 8, wherein the heartrate data of the user is categorized as workout when the user input to launch the application has been received and the application is configured to track the second action of the user.

13. The computer-implemented method of claim 8, wherein the first sensor is distinct from the second sensor.

14. The computer-implemented method of claim 8, wherein the action category is associated with a particular collection technique, and wherein collecting the heartrate data of the user comprises collecting the heartrate data of the user using the particular collection technique.

15. One or more non-transitory computer-readable media comprising computer-executable instructions that, when executed by one or more processors of a wearable device, cause the wearable device to perform operations comprising:

tracking a first action of a user wearing the wearable device using a first sensor of a plurality of sensors of the wearable device;

tracking a second action of the user using a second sensor of the plurality of sensors of the wearable device;

determining, on a user interface of the wearable device, whether a user input is received to launch an application of the wearable device has been launched;

determining an action category of the user based at least in part on the first action, the second action, and whether the user input to launch application has been received;

collecting heartrate data of the user;

categorizing the heartrate data into a heart rate data category based at least in part on the determined action category; and presenting, via the user interface, heartrate information corresponding to the categorized heartrate data.

16. The one or more non-transitory computer-readable media of claim 15, wherein the heartrate data of the user is collected based at least in part on the determined action category.

17. The one or more non-transitory computer-readable media of claim 15, wherein the heartrate data of the user is categorized as sedentary when the first action of the user is below a threshold and the user input to launch the application has not been received.

18. The one or more non-transitory computer-readable media of claim 15, wherein the heartrate data of the user is categorized as a breathing category when the user input to launch the application has been received and the application comprises breathing instructions for the user.

19. The one or more non-transitory computer-readable media of claim 15, wherein the heartrate data of the user is categorized as workout when the user input to launch the application has been received and the application is configured to track the second action of the user.

20. The one or more non-transitory computer-readable media of claim 15, wherein the first sensors is distinct from the second sensors.

* * * * *